United States Patent [19]

Scarrow

[11] Patent Number: 5,061,264

[45] Date of Patent: Oct. 29, 1991

[54] APPARATUS FOR CONTACTING MATERIAL SUCH AS A DRUG WITH A FLUID

[75] Inventor: David Scarrow, Norton St. Philip, United Kingdom

[73] Assignee: DRG Flexpak Limited, Bristol, England

[21] Appl. No.: 340,676

[22] PCT Filed: Mar. 31, 1988

[86] PCT No.: PCT/GB88/00256

§ 371 Date: Mar. 17, 1989

§ 102(e) Date: Mar. 17, 1989

[87] PCT Pub. No.: WO88/07358

PCT Pub. Date: Oct. 6, 1988

[30] Foreign Application Priority Data

Apr. 2, 1987 [GB] United Kingdom ................. 8707917

Feb. 12, 1988 [GB] United Kingdom ................. 8803324

[51] Int. Cl.[5] ........................ A61B 19/00; B65D 25/08

[52] U.S. Cl. .................................... 604/408; 604/409; 604/411; 604/414; 206/221

[58] Field of Search ................................ 604/411-415, 604/405, 406, 83, 86, 87, 88, 89; 206/221, 219, 220, 222

[56] References Cited

U.S. PATENT DOCUMENTS

| | | | |
|---|---|---|---|
| 2,585,938 | 2/1952 | Jordan | 604/415 X |
| 4,573,506 | 3/1986 | Paoletti | 604/415 X |
| 4,583,971 | 4/1986 | Bocquet et al. | 604/82 |
| 4,606,734 | 8/1986 | Larkin et al. | 604/84 |
| 4,614,515 | 9/1986 | Tripp et al. | 604/403 |
| 4,675,020 | 6/1987 | McPhee | 604/411 |
| 4,735,608 | 4/1988 | Sardam | 604/89 |
| 4,784,658 | 11/1988 | Grabenkort | 604/410 |
| 4,785,858 | 11/1988 | Valentini et al. | 604/415 X |

FOREIGN PATENT DOCUMENTS

| | | |
|---|---|---|
| 0117489 | 9/1984 | European Pat. Off. . |
| 8503432 | 8/1985 | World Int. Prop. O. . |

*Primary Examiner*—Robert A. Hafer
*Assistant Examiner*—Michael Brown
*Attorney, Agent, or Firm*—Larson & Taylor

[57] ABSTRACT

A drug delivery system for enabling liquid in a container (10) to contact the contents of a vial (48) employs a cup (22) having a mouth through which a vial (48) is insertable head down. A conduit (70, 26, 12) extends from the cup (22) interior to the container (10) interior, possibly via a non-release coupling (16, 18, 34, 36). A retainer (50) is non-releasably engageable (64, 44) with the cup (22) to trap a vial (48) therein and urge it against the conduit (70). The retainer (50) and cup (22) may engage threadedly (62, 38), with a ratchet (64, 44) preventing disengagement.

13 Claims, 4 Drawing Sheets

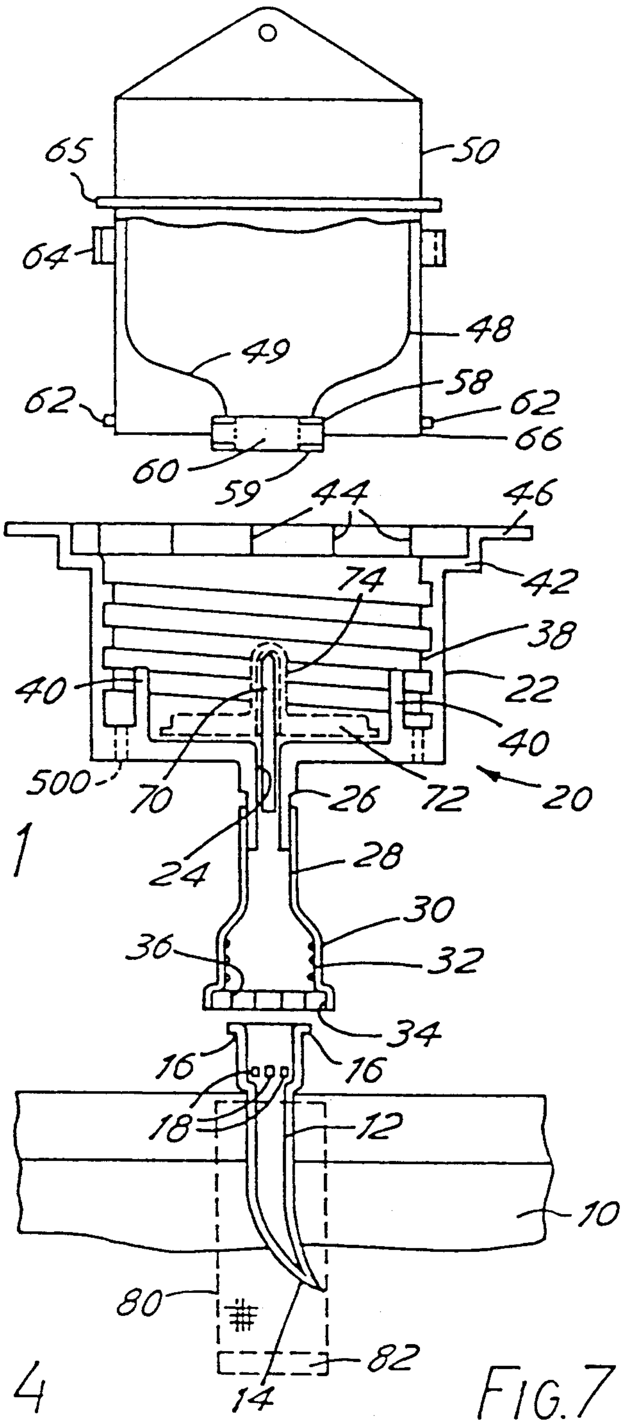
FIG. 1
FIG. 4
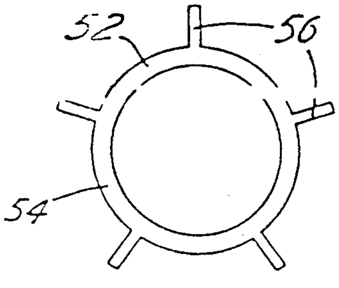
FIG. 7
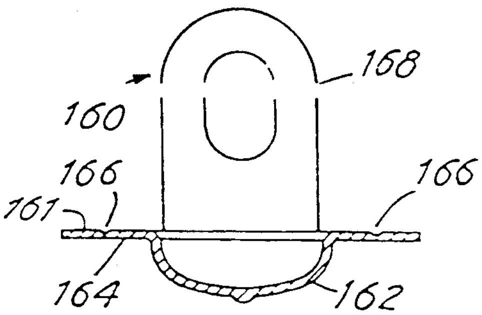

APPARATUS FOR CONTACTING MATERIAL SUCH AS A DRUG WITH A FLUID

BACKGROUND OF THE INVENTION

The present invention relates to apparatus for contacting material such as a drug with a fluid. It particularly relates to apparatus by means of which material can be contacted with a fluid in a closed system.

PCT Specification WO 85/03432 discloses a closed drug delivery system comprising a flexible container of fluid, a cup permanently coupled to the container, and a standard glass drug vial within the cup, which is permanently closed by a cap. The cap is deformable to urge the vial downwardly, whereby a spike at the end of a conduit leading into the container is urged into the vial. Thus liquid from the container can contact material in the vial.

This system has some disadvantages. It is a sealed unit, including the container of fluid and the vial of drug. Thus every possible combination of fluid and drug must be manufactured and stocked. A manufacturer who produces containers of fluid may not wish to involve himself with the cup portions and vials of drugs and in any case it would be desirable for the same containers to be usable in other manners.

It is desirable to sterilise the filled fluid container using steam, but steam sterilisation of the cup assembly can lead to problems. It is thus necessary to steam-sterilise only the filled container portion. This is then placed in a room with the remaining components, and they are all subjected to sterilisation using a sterilising gas. The unit is then assembled within the sterilising room. Not only is this double sterilisation inconvenient, but the usual sterilising gas, ethylene oxide, may become absorbed by or dissolved in plastics components. It may leak into the fluid. Even if this does not happen, it is necessary to leave the units in ventilated storage for some time so that gas that has been taken up or adsorbed can escape. Conventionally, medical articles are over-wrapped prior to sterilisation, but in this case only the container portion can be over-wrapped. Thus the cup portion may be contaminated during the steam sterilisation process and in subsequent handling.

The manufacture of a cup with a lid such that it can be used for pressing down a vial is relatively difficult and therefore expensive; and the operation of using the lid to press down a vial is not easy.

A given cup is only suitable for a single size and shape of vial.

The present invention enables one to ameliorate one or more of the above drawbacks.

SUMMARY OF THE INVENTION

In one aspect the invention provides apparatus for use in establishing flow communication between the interior of a vial and the interior of a container, said apparatus comprising cup means for receiving a dispensing end portion of a vial, said cup means having a mouth portion through which said end portion of a vial is insertable and conduit means communicating the interior of the cup means with the exterior, said conduit means being communicable with a container to establish said flow communication; and locking means operable to retain a vial non-removably with said end portion inserted in the cup means, the vial's interior then being communicable with the interior of a container via said conduit means. The apparatus may include retainer means engageable with said cup means to retain a vial. The retainer and cup means may be mutually adapted to permit their irreversible connection to retain a vial non-removably. Thus there may be complementary engagement means on the retaining means (which may constitute a lid for the cup means) and on the cup so that mutual engagement of lid and cup urges a vial deeper into the container; the locking means may act to prevent their disengagement. These means can take various forms. A simple arrangement is for the lid and cup to have respective ones of a ratchet and detent means, arranged to be mutually engageable but not disengageable. Alternatively there may be complementary ribs that can be pushed past one another in one sense but not withdrawn. The engagement means may employ a thread within the cup. The lid may then have an external thread or thread portions (e.g. lugs, e.g. as in a Luer lock). Alternatively or additionally, the locking means may comprise engagement means provided by the cup means for irreversibly engaging a vial.

Thus a large number of fluid/drug combinations are available from a moderate number of vials of different drugs and containers of different fluids. Once a vial has been brought into communication with the fluid, the assembly is locked together, so that the vial cannot be removed, which would allow adulteration of the contents of the container. More importantly, it would bring a risk of contamination.

Cup means may be permanently connected to a container. However, it is also possible for a container to have connecting means for coupling with complementary means associated with the cup. These may comprise a thread and a Luer lock. Preferably there are means for rendering their engagement irreversible, e.g. a ratchet arrangement similar to that described above. Storage of fluid containers can be more efficient when they are not coupled to the cups. A further way of permitting this is for the cup to have an external tubular spike portion so that it can be brought into communication with a container by pushing a spike through a penetrable stopper a rubber septum or the like provided by the container. Of course, unless means are provided for preventing withdrawal, this brings the risk associated with removable vials.

Spacers may be provided so that different types of vial can be used with the same cup. For example, the cup may have a cup-shaped lid into which vials can be fitted, with the interposition of spacer means as required.

In different aspects the invention provides an assembly comprising a cup and a container, coupled or couplable together; a cup adapted to be coupled to a container; a container adapted to be coupled to a cup; and a method of contacting a material such as a drug with a fluid.

BRIEF DESCRIPTION OF THE DRAWINGS

FIG. 1 is a schematic sectional view of apparatus embodying the invention;

FIG. 4 is a plan view of a first type of spacer member;

FIG. 7 is a sectional view of a diaphragm assembly;

DESCRIPTION OF THE PREFERRED EMBODIMENTS

Figure 2:
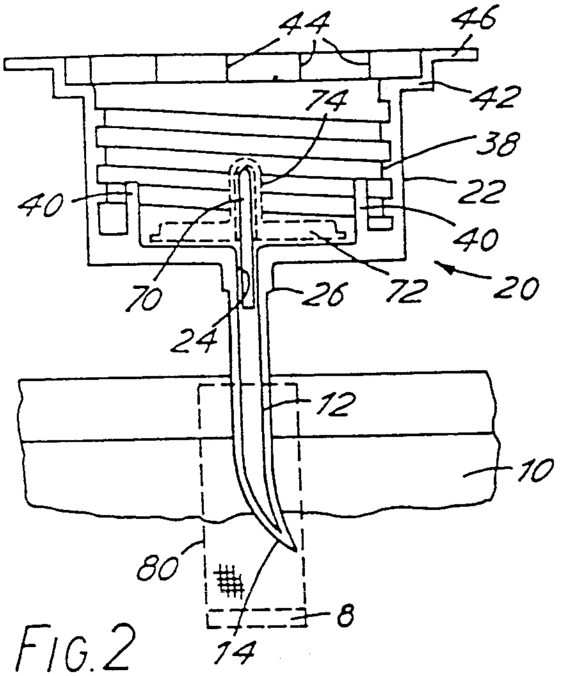
FIG. 2 is a detail of a modified embodiment.

A sterile fluid container 10 has a conduit 12 extending from the interior to the exterior. At the interior, it is closed by a breakable seal 14. At the outer end, it has the external formations 16 of a Luer lock. A little way beneath these, there are some detents 18, which are small flexible vanes.

The conduit 12 may be provided with a filter to trap any debris produced by breaking the seal. As shown in FIGS. 1 and 2, this may comprise a filter sheath 80 about the end portion of the conduit 12. This may be provided by a flat tube of filter material, e.g. nylon mesh, sealed at its lower end region 82. The upper end region of the sheath may be sealed into the container 10 by the sealing step that forms the upper seal 74 of the container.

Figure 3:
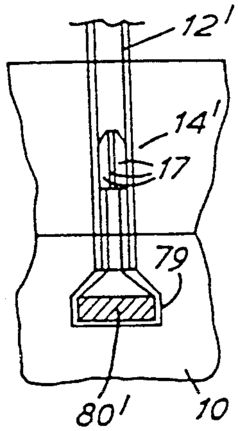
FIG. 3 is a detail of a modified conduit.

FIG. 3 shows an alternative form of conduit 12'. This has an internal breakable barrier 14' of known type (employing axial vanes 17). Downstream of this, a widened portion 79 of the conduit houses a porous disc filter 80'. Alternatively the filter 80' can be housed in a separate tube portion which is attached to the end of the conduit.

A cup assembly 20 includes a plastics cup member 22. In the base thereof there is a central opening 24, which extends outwardly through a spigot portion 26. A short conduit 28 is sealed to this, and terminates in a socket portion 30 having an internal thread 32 for engaging the Luer lock formations 16. The socket portion 30 has an enlarged mouth portion 34 within which there are ratchet teeth. The arrangement is such that the socket portion 30 and conduit 12 can be screwed together. Finally the detents 18 engage the ratchet teeth 36, which prevent unscrewing.

FIG. 2 shows a variant in which the cup assembly 20 is permanently connected to the fluid container 10. In effect, the spigot portion 26 has been extended and made integral with the conduit 12 that is sealed into the container 10.

The cup member 22 has an internal thread 38. A short cylindrical wall 40 extends axially from the base, a short distance radially within the thread 38. The upper mouth region of the cup 22 has an enlarged mouth portion 42, which is formed with ratchet teeth 44. Finally, there is a peripheral flange 46.

A vial 48 is housed within a housing 50. As shown, the vial 48 fits snugly within the housing 50, abutting the end thereof such that the mouth of the vial 48 projects slightly beyond the housing 50. To enable the same housing 50 to be used with differently dimensioned vials, spacers may be employed. FIG. 4 shows a spacer 52 which is an annulus 54 with five equispaced ribs 56 dimensioned to contact the inner wall of the housing 50. For use with a short vial 48, the spacer may itself be cup-shaped to take up the excessive length.

Figure 5:
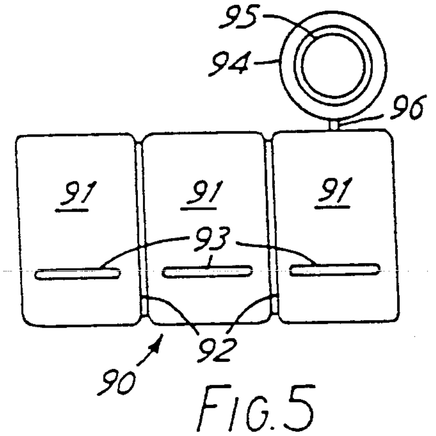
FIG. 5 is a view of an assembly for providing a second type of spacer member.
Figure 6:
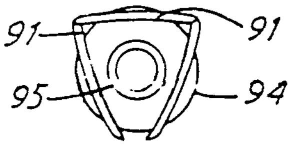
FIG. 6 is a view of the second type of spacer member.

We have found that glass vials of the same nominal size actually vary quite widely, so there is a risk that an over-sized vial will not fit into an annular spacer 52. FIGS. 5 and 6 show a spacer assembly having a wide tolerance. An injection-moulded plastics blank 90 has three rectangular panels 91 hinged together in a row by thinned regions 92. Each panel has a transverse slot 93. A disc 94 with an annular rib 95 is connected to one panel 91 by a nib 96. For use, the disc 94 is snapped off and the array of panels is folded to define approximately a trigonal prism, within which a vial may be housed. Depending on the length of the vial, the disc 94 may be omitted or mounted in the slots 93 to provide an end wall. The effective depth of the vial housing is variable by orienting the disc with the rib projecting upwardly or downwardly. Of course, a plurality of sets of slots 93 may be provided.

The vial 48 is of conventional type, having a neck 49 leading to a mouth with an annular rim. The mouth is closed by a cap 58 with an aluminum collar 59 engaged over the rim, and a penetrable rubber septum 60.

The housing 50 has lugs 62 adjacent its open lower end. These are threadedly engageable with the thread 38 within the cup member 22. At an intermediate region, the housing 50 has tangentially projecting external vanes 64. Just above them, there may be an annular flange 65. Thus, when the housing 50 is screwed into the cup member 22, this is initially reversible. However, towards the end of its travel, the vanes 64 engage the ratchet 44, and the engagement becomes irreversible. The engagement becomes still more firm and positive because a mouth region 66 of the housing becomes engaged between the outer wall of the cup 22 and the cylindrical wall 40. If the flange 65 is present, it covers the ratchet means 44,64 thus making it still more difficult for someone to force disengagement.

The cup member contains a tubular spike 70 which passes sealingly through the aperture 24. This is dimensioned so that, when a housing 50 containing a vial 48 is screwed into the cup member 22, the spike 70 is driven through the rubber septum 60 into the interior of the vial 48. This does not occur until the vanes 64 engage the ratchet 44. There may be a rubber gasket 72 on the base of the cup, against which the vial is sealingly and resiliently urged. A sheath portion 74 may initially cover the spike 70, and be ruptured by the vial.

Thus, in use, an appropriate vial and an appropriate receptacle 10 of fluid are selected. The rubber septum 60 of the vial is swabbed with a sterilising fluid. The cup assembly 20 is secured irreversibly to the container 10. The vial is engaged in the housing 50, using a spacer if necessary. The housing 50 is then screwed down into the cup member 22, so that the spike 70 is urged into the vial. Then, the sealed end 14 of the conduit 12 can be snapped off. Now, the interior of the receptacle 10 and the interior of the vial 48 are in flow communication. This has been achieved under normal aseptic handling conditions, and the arrangement is tamper-proof. Fluid can be pumped from the receptacle 10 into the vial 48 and back again by squeezing the receptacle 10, in generally known fashion.

Particulate contamination produced by breaking the seal (14 or 14') or particulate material from the cup member 22, e.g. undissolved drug particles, will be filtered out by the filter (80 or 80').

Instead of (or in addition to) the provision of spacers, a range of different housings may be provided. Thus FIGS. 9 A–D show housings 190 formed in two parts: a standard lower portion 192, providing the ratchet vanes 64 and the screw lugs 62; and an upper portion 194 which provides the base 196 and a suspension loop 198. A flange 65 can be provided at the zone of connection. The different upper portions 194 are adapted to different lengths and diameters of vials.

The cup assembly may be sealed for storage under sterile conditions. Thus there may be a peelable diaphragm across the cup mouth, and a similar or different seal across the lower mouth 34.

Figure 12:
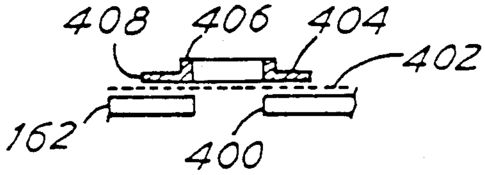
FIG. 12 is a schematic sectional view showing an aperture with controlled porosity.

A conventional peelable diaphragm across the cup mouth may give rise to problems, e.g. if paper tear brings a risk of particulate contamination of the cup interior. Thus we may employ a diaphragm assembly 160 which provides a clean tear. A suitable assembly is shown in FIG. 7. It may be injection moulded from PVC optionally blended with a nitrile rubber. An annular outer portion 161 may be welded to the flange 46 to close the open mouth of the cup member 22. The illustrated assembly 160 has a circular disc having a central depressed portion 162 and an outer flange 164. In an intermediate region the flange 164 has an annular "thinned" region 166 which forms a tear line. A finger pull tab 168 may be formed on the flange inwardly of the thinned region 166. In use, this is pulled to tear away the assembly within the thinned region 166, leaving a cleanly exposed cup member 22. It has been found that, during autoclaving, the external pressure may force the central portion 162 down into the cup so far that it may be damaged by the spike 70. It may be shaped to minimise this risk, e.g. being connected to the flange 164 via an annulus that extends upwardly from the flange 164. Alternatively or additionally, the diaphragm may have a porous region for preventing the formation of large pressure differences across it. This may be provided as shown in FIG. 12. An aperture 400 is provided in the central portion 162. A filter membrane 402 is laid over it, and a plastics annular washer 404 is placed on the membrane. The washer may have a flat flange portion 408 with a raised rib 406 surrounding the aperture. The flange portion 408 of the washer is sealed to the central portion 162 of the diaphragm through the membrane 402 by a suitable technique, e.g. RF, heat or ultrasonic welding, depending on the materials involved. The filter membrane 402 is selected to provide sufficient porosity while still serving as a barrier to microorganisms. For example it may be a filter medium of nylon-6,6 (e.g. as available under the trademarks Ultipor and Posidyne from Pall Process Filtration Ltd.), e.g. with a pore size of 2 $\mu$m.

Figure 8:
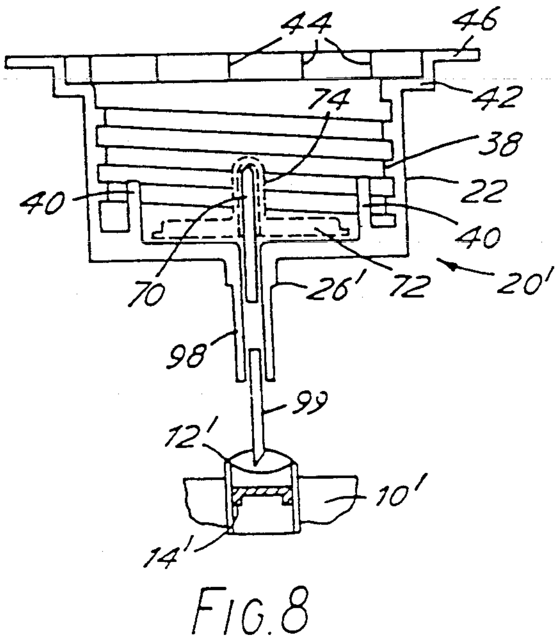
FIG. 8 shows a further form of cup assembly.
Figure 9A:
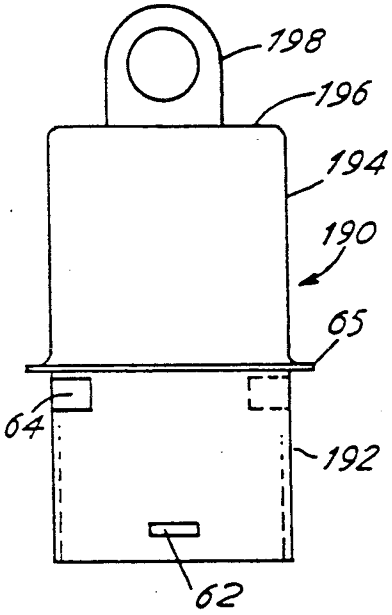
FIG. 9 A,B,C and D show alternative housings.
Figure 9B:
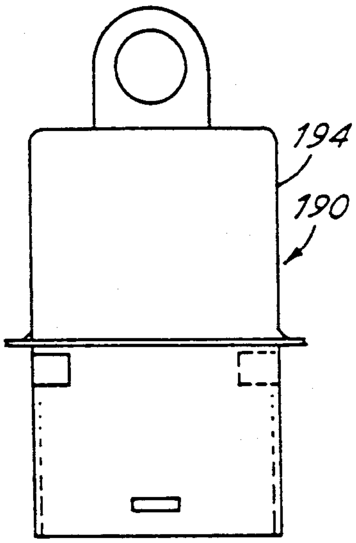
Figure 9C:
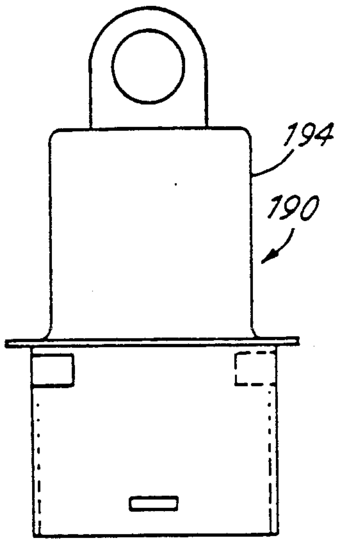
Figure 9D:
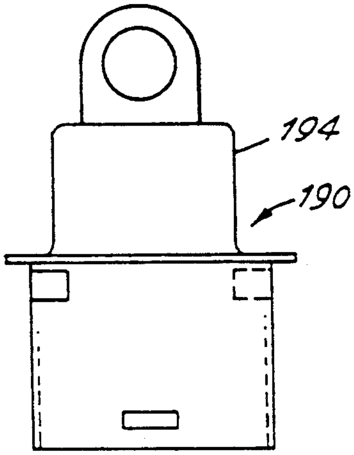

FIG. 8 shows a modified cup assembly 20', differing from that shown in FIG. 1 in that the spigot portion 26' terminates in a conduit portion 98 carrying a tubular spike 99. Thus the cup assembly 20' (when containing a vial) can be coupled to a fluid container (shown schematically at 10') by pushing the spike through an administration port 12' (generally having a penetrable septum 14') of the container.

Figure 10:
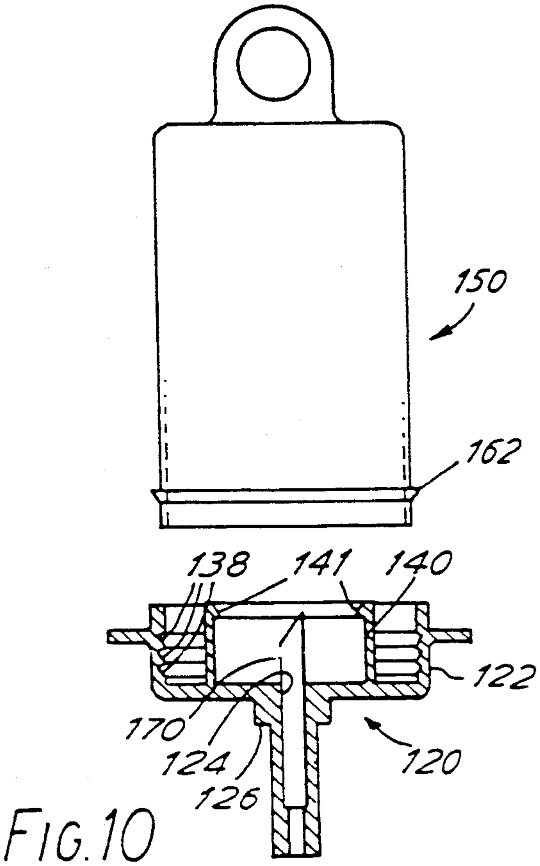
FIG. 10 shows a further embodiment of the invention.

FIG. 10 shows another embodiment. The cup assembly 120 includes a plastics cup member 122 of smaller axial extent. Its central opening 124, spigot portions 126 etc. may be as previously described, and are open to similar modifications.

Again there is an inner cylindrical wall 140, but this is of smaller diameter and has, in its upper region, an inwardly projecting detent bead 141. This is so dimensioned (and positioned relative to the spike 170) that when a vial 48 (as shown in FIG. 1) is pushed on, as the spike 170 is forced through the septum 60, the cap 58 is forced past the detent bead 141. This bead is shaped so that the inward passage of the cap 58 is relatively easy, but it is then trapped. (This can be enhanced if the cap 58 is given a complementary shape.) It may not then be essential to use a housing 150, so that the form of the cup assembly could be simplified. However for greater security, use of a housing is still recommended. This example shows a different form of engagement: the inner cylindrical face of the cup member 122 has ribs 138 of sawtooth section, and the housing 150 has a complementary rib 162.

Thus the housing can be pushed into the cup member 122, and its rib 162 clips behind one or more ribs 138 of the cup member 122 and is, for practical purposes, unreleasable. This is achieved more simply than in the FIG. 1 embodiment which requires not only threaded engagement means 62,38 but also the relatively elaborate ratchet means 64,44. Of course, this form of detent means is not restricted to this embodiment. Ribs (162 and/or 138) could be replaced by projections.

Figure 11:
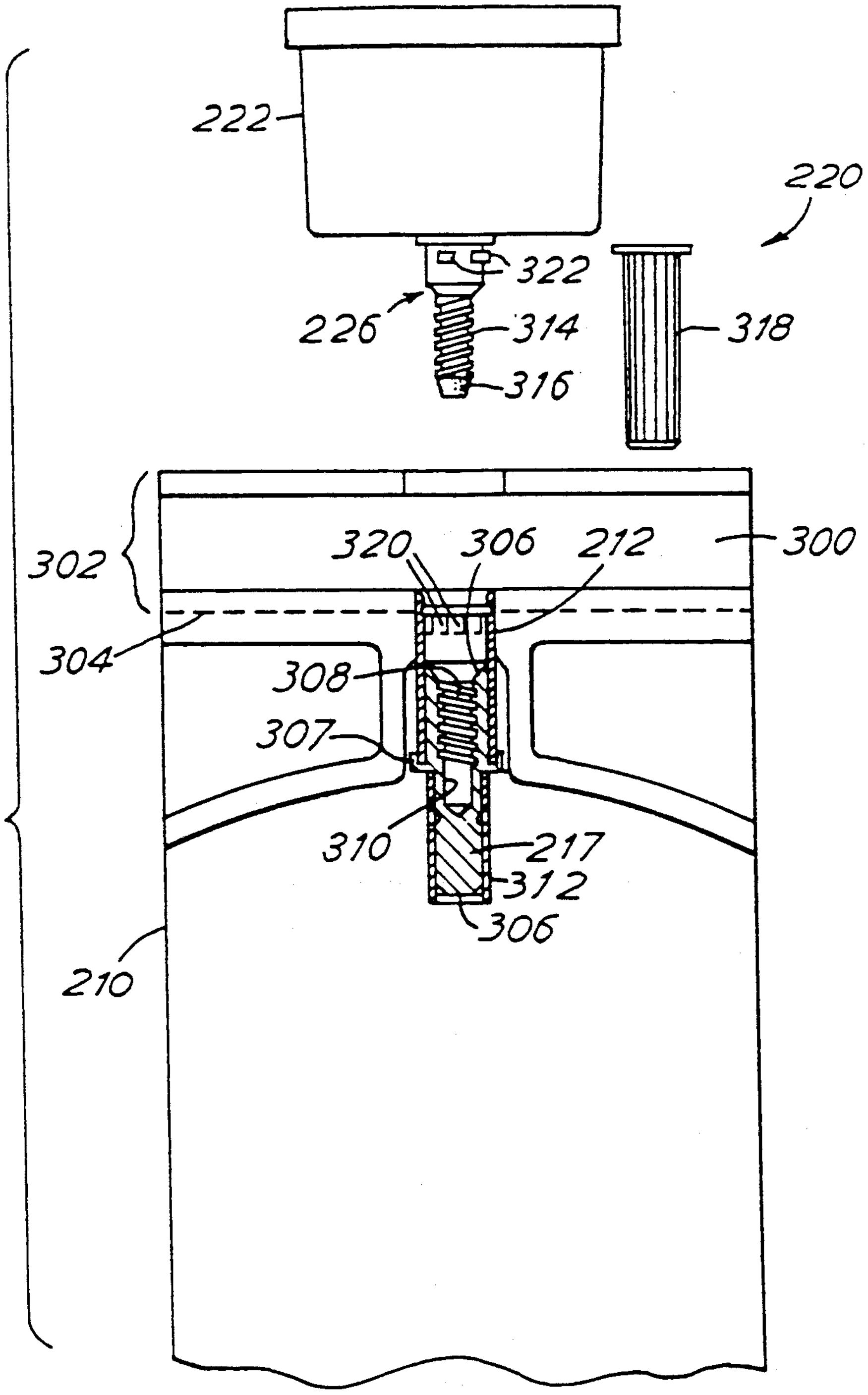
FIG. 11 shows details of a still further embodiment of the invention.

FIG. 11 shows fluid container 210 and cup assembly 220 of a further embodiment of the invention. The container 210 has a conduit 212 extending into its interior. Initially the exterior of the conduit 212 opens in an expansion chamber 300. This is provided by an end portion 302 of the container delimited by a tear line 304 so it can be torn away to expose the end of the conduit 212. An insert 306 of polycarbonate plastics material projects from the inner end of the conduit 212. It is initially just a push-fit within the conduit, its degree of insertion delimited by a flange 307, but becomes bonded during heat sterilisation. The insert 306 provides (from the outer end) an internally threaded portion 308, a location taper 310 (of standard Luer type), and a breakable barrier 217 which closes the conduit 212. A lower conduit portion 312 is pushed over the projecting lower part of the insert 306 to retain the broken off part of the barrier 217 when it is snapped. The lower conduit portion 312 may have apertures to facilitate flow once the barrier 217 is broken.

The cup assembly 220 comprises a cup member 222 (possibly of K resin) which may be generally as any previously described. Its base has a central spigot 226. This has an external thread 314 complementary to the threaded portion 308 of the insert in the container 210. (They may be two-stage threads to give rapid engagement.) An end portion 316 of the spigot 226 has an external taper complementary to the location taper 310. The spigot 226 may initially be protected by a disposable cover 318.

For use, the conduit 212 and spigot 226 are exposed by removal of the expansion chamber 300 and cover 318. The spigot 226 is screwed into the insert within the conduit until the tapered portions 310,316 engage. Locking means prevent disengagement. Thus there may be ratchet teeth 320 within an outer portion of the conduit for irreversible engagement with tangentially projecting vanes 322 on an upper portion of the spigot 226.

Apparatus embodying the invention is also useful in the field of blood products. Thus we may provide an unfilled fluid container 10 coupled with a cup assembly (e.g. 20), with a housing (e.g. 50) inserted partially (and therefore removably) into the cup member; the whole assembly being sealed in a pouch and sterilised, suitably by gamma irradiation or steam sterilisation. Use of steam sterilisation under pressure may tend to cause the housing 50 to become deformed. This can be avoided by providing the housing 50 or cup member 22 with controlled gas permeability. In one form, the housing 50 is provided with a porous region as described above with reference to FIG. 12 for the cup diaphragm 160. Such a filter membrane 402 allows steam to gain access to the interior of the housing, even if its open end is closed by insertion into the cup member 22. For use it is removed from the pouch and the container is filled with (e.g.) blood plasma. The housing is removed to enable a vial of medicament to be selected, inserted, and brought into contact with the plasma by means of the assembly.

In an alternative form, one or more apertures 500 (FIG. 1) are provided in the base of the cup member 22, in the region between the side wall of the cup and the inner cylindrical wall 40. Thus, when a housing 50 is inserted partially into the cup member 22, gases (e.g. air and steam) can pass into and out of the interior of the cup assembly 20 via the apertures 500. When a housing 50 (containing a vial 48) is moved into its final, operable position (from which it cannot be withdrawn), the apertures 500 are closed by the leading edge of the housing 50.

I claim:

1. Apparatus for use in contacting with a fluid a medicament which is in a vial of standard type, the vial including a body having an interior for holding the medicament, the body having a rear end portion, a dispensing end portion with a mouth communicating the interior to the exterior, a penetrable rubber stopper closing off the mouth, and means for retaining the stopper sealingly on the vial body, said apparatus comprising, cup means having a cup base and a cup wall which define a cup interior and a mouth portion, said cup interior being dimensioned to receive the dispensing end portion of a vial, said cup means including conduit means extending through said cup base for communicating the interior of the cup means with the exterior thereof, said conduit means having at the cup interior a tubular spike extending towards the mouth portion of the cup so as to contact the rubber stopper of a vial when the dispensing end portion thereof is received in the cup interior, said conduit means having at the exterior of the cup means, means for effecting fluid flow communication with a container of fluid, a cylindrical shaped housing having an open mouth at one end thereof and an end wall at the opposite end thereof, said cylindrical shaped housing adapted to receive the vial through the open mouth, retainer means on the outer surface of said housing, engagement means on said cup for engagement with said retainer means whereby the housing may be displaced in the axial direction of the cup means towards the cup base, said engagement means including locking means to lock the housing permanently to the cup means when the relative axial displacement of the housing towards the cup base exceeds a predetermined extent, whereby when the vial and housing for the vial are urged towards the cup base, said cup means and said housing are so dimensioned that said tubular spike is forced through the rubber stopper on the vial so that the vial interior is in flow communication with the conduit means, and the locking means locks the housing permanently to the cup means whereby the vial is locked in place with the interior of the vial in flow communication with said conduit means.

2. Apparatus according to claim 1 wherein said engagement means include complementary threaded engagement means on the retainer means and cup means; and said locking means comprise ratchet means on the housing and cup means which are engageable to permit threaded engagement of said threaded engagement means but to restrain threaded disengagement thereof.

3. Apparatus according to claim 2 wherein the threaded engagement means and ratchet means are so arranged that the threaded engagement means are engageable over a run having first and second portions in succession; engagement in the second portion causing engagement of the ratchet means to restrain threaded disengagements, whereas engagement in the first portion is reversible without restraint by the ratchet means.

4. Apparatus according to claim 1 wherein said engagement means on the retainer means and said cup comprise annular ribs of sawtooth cross section on one of said housing and cup and at least one complementary rib or projection on the other of said housing and cup.

5. Apparatus according to claim 1 wherein said housing comprises a cylindrical sleeve for embracing a vial and said cup means includes an annular cup wall and a coaxial internal annular wall adjacent the conduit means, the housing being displaceable to a configuration in which said sleeve projects snugly between the annular cup wall and the coaxial internal annular wall.

6. Apparatus according to claim 1 wherein the housing includes a cylindrical sleeve for embracing a vial and at least one spacer dimensioned to fit snugly within the sleeve and adapted to hold a vial which would otherwise be a loose fit within the sleeve.

7. Apparatus according to claim 1 wherein said conduit means has an exterior end portion adapted to be coupled to second conduit means operatively associated with a container.

8. Apparatus according to claim 1 including a diaphragm closing the mouth portion of the cup means, said diaphragm having a portion adapted to be torn away to permit engagement of said retainer means and a vial.

9. Apparatus according to claim 1 wherein said conduit means terminates exteriorly of the cup means in a tubular spike.

10. Apparatus according to claim 1 further including a container for a liquid, said conduit means being communicable with the interior of the container.

11. Apparatus according to claim 10 wherein the conduit means comprises a first conduit means communicating with the interior of the cup means and a second conduit means communicating with the interior of the container; said first and second conduit means having complementary coupling fittings to permit coupling and to restrain uncoupling.

12. Apparatus according to claim 10 wherein the container has a conduit portion for flow communication; said container conduit portion having frangible means to prevent flow communication until said frangible means is broken.

13. Apparatus according to claim 12 including a particulate material retaining member arranged to trap particulate material generated by breaking said frangible means.

* * * * *